United States Patent [19]

Flory

[11] Patent Number: 4,677,848

[45] Date of Patent: Jul. 7, 1987

[54] MULTI-SIZE TIRE CHUCK

[75] Inventor: Thomas A. Flory, Akron, Ohio

[73] Assignee: Monsanto Company, St. Louis, Mo.

[21] Appl. No.: 803,755

[22] Filed: Dec. 2, 1985

[51] Int. Cl.$^4$ .......................................... G01M 17/02
[52] U.S. Cl. .................................................... 73/146
[58] Field of Search ............................ 73/146, 487, 484

[56] References Cited

U.S. PATENT DOCUMENTS

| | | | |
|---|---|---|---|
| 2,163,469 | 6/1939 | Raschka | 144/288 |
| 2,390,008 | 11/1945 | Sherwood et al. | 144/288 |
| 2,695,520 | 11/1954 | Karsai | 73/146 |
| 3,375,714 | 4/1968 | Bottasso | 73/146 |
| 3,464,264 | 9/1969 | French | 73/146 |
| 3,550,443 | 12/1970 | Sherkin | 73/146 |
| 3,552,200 | 1/1971 | Hermanns et al. | 73/146 |
| 3,656,343 | 4/1972 | Braden et al. | 73/146 |
| 3,728,542 | 4/1973 | Golfier | 250/52 |
| 3,789,226 | 1/1974 | Green et al. | 250/360 |
| 3,801,786 | 4/1974 | Neuhaus | 250/360 |
| 3,895,518 | 7/1975 | Leblond | 73/146 |
| 3,948,094 | 4/1976 | Honlinger | 73/146 |
| 4,023,407 | 5/1977 | Vanderzee | 73/146 |
| 4,380,927 | 4/1983 | Oda et al. | 73/146 |

Primary Examiner—Donald O. Woodiel
Attorney, Agent, or Firm—Gordon B. Seward

[57] ABSTRACT

A tire chuck is disclosed which is designed with stepped ridges so as to accommodate a range of tire sizes, and is constructed of a material which is deformable and is relatively transparent to, and not degraded by x-rays.

5 Claims, 3 Drawing Figures

MULTI-SIZE TIRE CHUCK

BACKGROUND OF THE INVENTION

This invention relates to a chuck for holding a pneumatic tire, which chuck is designed to hold a range of tire sizes. The tire is held in the chuck under pressure and can be subjected to any of a variety of operations, such as inspection, balancing, grinding and the like.

A number of chucking devices have been developed in the past which were designed to hold a tire for inspection or some other operation. Some of these devices, such as that of Neuhaus U.S. Pat. No. 3,801,786, are capable of accepting only a single size tire, and differing hubs must be mounted when different size tires are to be inspected.

Others, such as that of Golfier U.S. Pat. No. 3,728,542, show stepped opposing chuck members, which accept different tire sizes. The members, however, are rigid metal, incapable of flexure and opaque to x-rays. Sherkin U.S. Pat. No. 3,550,443 shows a similar device with the same limitations.

Honlinger U.S. Pat. No. 3,948,094 discloses a similar tire chuck device in which a tire is held between flat surfaces for inspection during inflation. The flat surfaces are rigid metal plates, with a rubber covering.

SUMMARY OF THE INVENTION

The instant invention provides a device for holding a pneumatic tire under internal inflation pressure by means of two opposing frusto-conical members which are made from a deformable, semi-rigid material which is relatively transparent to x-rays and not easily degraded thereby. The members each have a plurality of stepped ridges shaped to conform to the bead portion of a tire, and sized to accommodate a plurality of standard bead diameters.

The members preferably have a substantially constant thickness through the series of stepped ridges so as to present a relatively constant mass when x-rays are passed therethrough, and also to provide the degree of flexibility desired when inflation pressure in a tire mounted thereon exerts axially outward pressure in the bead area.

BRIEF DESCRIPTION OF THE DRAWINGS

A more complete understanding of the invention may be obtained by reference to the drawings.

DESCRIPTION OF THE PREFERRED EMBODIMENT

Figure 1:
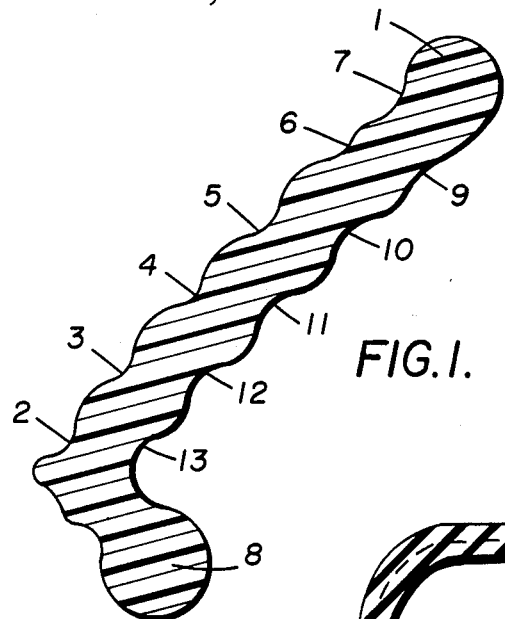
FIG. 1 is a cross-section of one of the members.

Referring to FIG. 1, a cross-section of one member is shown, indicated generally 1, with tire bead receiving ridges indicated 2, 3, 4, 5, 6, 7 which are shaped to conform to the axially outer portions of the beads of tires (not shown) of progressively larger radial diameter and progressively larger axial separation. A lobe 8 is located at the radially centermost portion of the member, shaped to be gripped and held by a hub member (not shown). Relieved portions 9, 10, 11, 12 and 13 of the member are located with respect to the ridges and opposite thereto so as to give the tire-receiving portions of the member a relatively constant cross section thickness.

It will be seen that the geometry of the member 1 is such that axially outward pressure by the bead of a tire (when mounted thereon under internal inflation pressure) will tend to deflect the member axially away from the bead, but the frusto-conical shape of the member also acts to counter such deflection, the radially outer portions of the member then being in compression.

Figure 2:
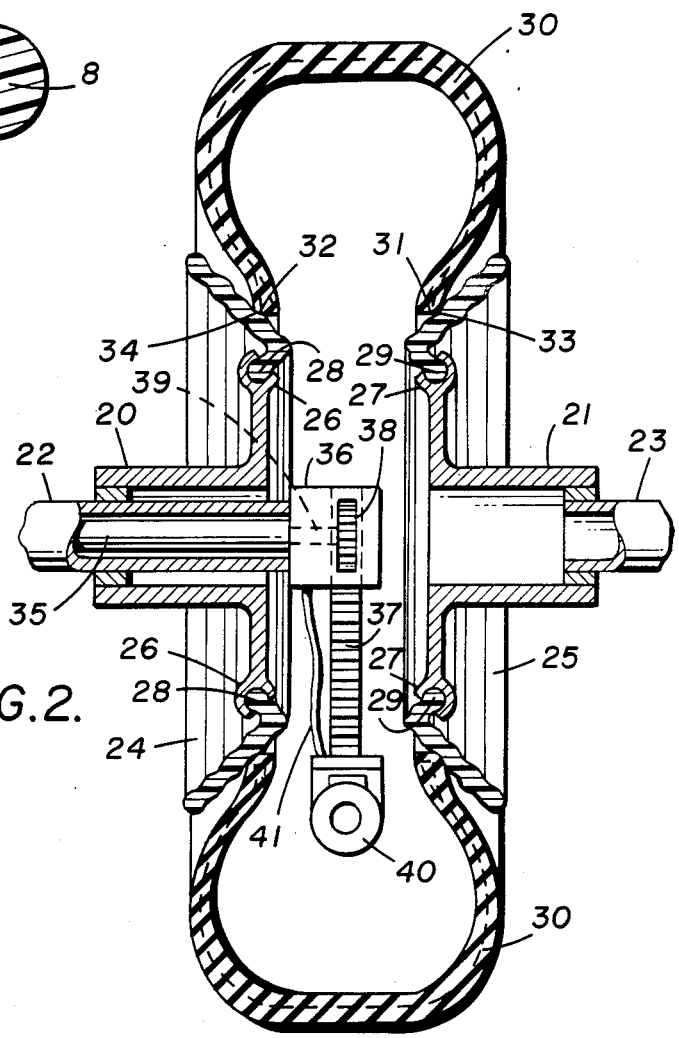
FIG. 2 is a partially sectioned view of the device held in position with a tire mounted thereon.

Referring to FIG. 2, a preferred device is shown, in which opposing hub members 20 and 21 are shown mounted for rotation, respectively, on hollow shafts 22 and 23. Shafts 22 and 23 are held on their opposite ends by frame members (not shown) with associated bearings and drive mechanism, also not shown. Members 24 and 25 are shown, held by gripping portions 26 and 27 of hub members 20 and 21, the gripping portions 26 and 27 being disposed about the lobes 28 and 29 of the respective members 24 and 25. A pneumatic tire 30 is shown held between the outer portions of members 24 and 25, with the bead portions 31, 32 of tire 30 in sealing contact with stepped ridges 33 and 34 of members 25 and 24 respectively. Internal air pressure can be introduced through the hollow central portions of either of the hubs and shafts. Shaft 35 is concentric with, and inside shaft 22. Shaft 35 supports member 36, which, in turn contains a rack- and pinion support for an x-ray source. The rack 37 extends slidably through member 36 and is extended and retracted by the rotation of pinion 38, which is actuated by shaft 39, extending back through the center of shaft 35. X-ray source 40 is mounted on end of rack 37, shown in FIG. 2 in its fully extended position. Power is supplied to source 40 through connector 41. In its fully outward position, source 40 can direct x-ray radiation outward through any portion of the tire, from bead to bead, to a receiving mechanism located outside the tire (not shown). The tire and the x-ray devices can be rotated relative to one another, so that complete inspection of the tire can be accomplished in a single rotation, if desired. Since the members are relatively transparent to x-rays, no difficulty is experienced, even in the bead areas, in obtaining an accurate x-ray picture of the tire construction.

Figure 3:
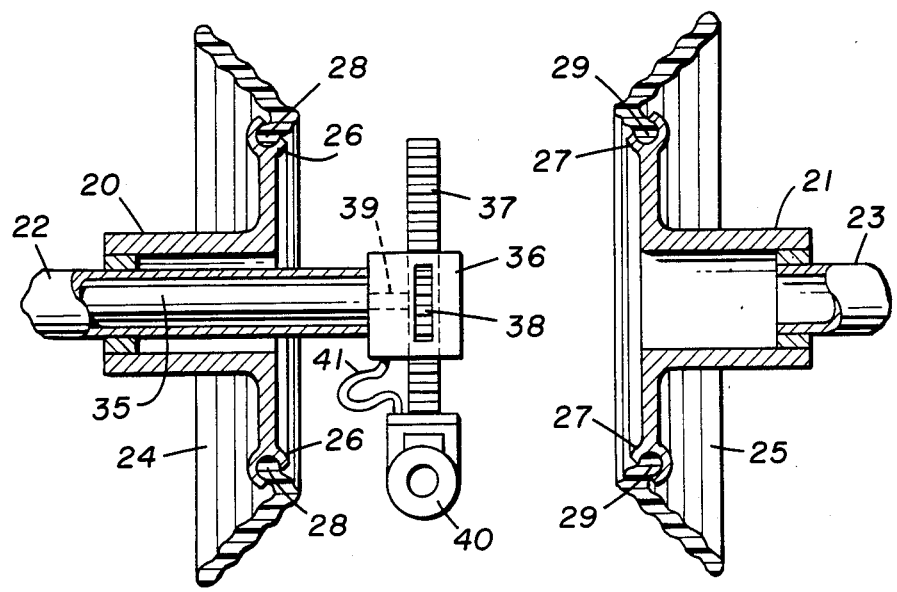
FIG. 3 is a partially sectioned view of the device without a tire mounted thereon.

FIG. 3 shows the preferred embodiment of the device, with no tire mounted thereon, and with the members axially separated from their positions in FIG. 2. In this view, rack 37 has been moved radially upward through member 36, so that rack 37 and x-ray source 40 are radially within the plane of the radially innermost ridges of members 24 and 25, enabling a tire to be mounted and demounted.

It should be understood that although the members are shown, as in FIGS. 2 and 3, mounted in a device for x-ray inspection of a tire, the members can be used to hold a tire under inflation pressure for any other desired purpose, such as balancing, or examination by other means.

In a more preferred embodiment of the invention, the members are formed from a material which combines optimum properties of density, hardness, x-ray transparency and resistance to the degrading effect of x-rays.

It has been found that a particular combination of a density of from 1.15 to 1.25, a hardness of from 40 to 72 (Shore D) and good resistance to x-rays is realized in certain thermoplastic polyester elastomers, including such materials sold by E. I. du Pont de Nemours & Company under the trademark "Hytrel." Other materials which have the required properties, as stated above, are also acceptable, as well, for the composition of the members.

I claim:

1. A device for holding a pneumatic tire under internal inflation pressure comprising two opposing frusto-conical members
    (A) made from a deformable, semi-rigid material relatively transparent to, and not easily degraded by, x-rays, and
    (B) having a plurality of stepped ridges shaped to fit the axially outer portion of a tire bead and sized to accommodate a plurality of standard bead diameters, said device also including means holding the members in a spaced, opposing position relative to each other, said means mounted for rotation about the central axes of the members.

2. The device of claim 1, wherein the members have a substantially constant thickness through the area of the stepped ridges.

3. The device of claim 1, wherein the members are made from a material having a density of from 1.15 to 1.25 and a Shore D hardness of from 40 to 72.

4. The device of claim 3, wherein the members are made from an elastomeric thermoplastic polyester.

5. The device of claim 1, also including means for x-ray inspection of a tire mounted thereon, comprising an x-ray source and an x-ray receiving device.

* * * * *